United States Patent
Liou et al.

(10) Patent No.: US 10,561,699 B2
(45) Date of Patent: Feb. 18, 2020

(54) METHOD FOR TREATING DIABETIC RETINOPATHY

(71) Applicant: HAN SHENG PHARMTECH, INC., Pingtung County (TW)

(72) Inventors: Shorong-Shii Liou, Pingtung County (TW); I-Min Liu, Pingtung County (TW); Kun-Yi Hong, Pingtung County (TW)

(73) Assignee: Han Sheng Phamtech, Inc., Pingtung, Pingtung County (TW)

( * ) Notice: Subject to any disclaimer, the term of this patent is extended or adjusted under 35 U.S.C. 154(b) by 447 days.

(21) Appl. No.: 15/480,975

(22) Filed: Apr. 6, 2017

(65) Prior Publication Data
US 2017/0209516 A1    Jul. 27, 2017

Related U.S. Application Data

(62) Division of application No. 14/632,653, filed on Feb. 26, 2015, now abandoned.

(51) Int. Cl.
*A61K 36/00* (2006.01)
*A61K 36/8984* (2006.01)
*A61K 36/481* (2006.01)
*A61K 36/232* (2006.01)

(52) U.S. Cl.
CPC ........ *A61K 36/8984* (2013.01); *A61K 36/232* (2013.01); *A61K 36/481* (2013.01); *A61K 2236/33* (2013.01); *A61K 2236/331* (2013.01); *A61K 2236/333* (2013.01)

(58) Field of Classification Search
None
See application file for complete search history.

(56) References Cited

U.S. PATENT DOCUMENTS

| | | | | |
|---|---|---|---|---|
| 4,886,666 A * | 12/1989 | Liu | ....................... | A61K 31/715 424/764 |
| 2004/0161524 A1* | 8/2004 | Sakai | ................... | A61K 36/185 426/655 |
| 2004/0234633 A1 | 11/2004 | Kim et al. | | |
| 2005/0147699 A1 | 7/2005 | Wu et al. | | |
| 2011/0300246 A1* | 12/2011 | Huang | .................. | A61K 36/40 424/758 |
| 2013/0164396 A1 | 6/2013 | Liou et al. | | |

OTHER PUBLICATIONS

Wojcikowski et al. (201 0) Phytother. Res. 24: 875-884.
Agyemang et al. (2013) Evidenced-Based Complementary and Alternative Medicine, vol. 2013, Article ID 654643, 9 pages.
Duan et al. (2011) Medicinal Plant, 2(8): 58-60.
Li et al. (2004) Journal of Ethnopharmacology 92: 1-21.
Li et al. (2009) Molecules, 14, 5349-5361.
Mao et al. (2009) Phytomedicine 16: 416-425.
Pan et al. (2014) International J. Biological Macromolecules, 64: 420-427.
Tang et al. (2006) Phytother. Res. 20, 1046-1051.
Wu et al. (2013) Journal of Food Processing and Preservation, 37: 371-379.
Xing et al. (2013) Bioactive Carbohydrates and Dietary Fibre 1.2: 131-147.
Yin et al. (2009) Korean Journal of Pharmacognosy, (English Abstract).
Zhang et al. (1990) J. Ethnopharmacology, 30: 145-149.

* cited by examiner

*Primary Examiner* — Russell G Fiebig
(74) *Attorney, Agent, or Firm* — Muncy, Geissler, Olds & Lowe, P.C.

(57) ABSTRACT

A herbal composition for relieving symptoms of diabetic retinopathy includes 40 wt % of an ethanol extract of *Astragalus membranaceus*, 8 wt % of an ethanol extract of *Angelica sinensis* and 52 wt % of a water extract of *Dendrobium officinale*. A method for diabetic retinopathy by administrating the herbal composition to a subject in need is also provided.

2 Claims, 3 Drawing Sheets
(2 of 3 Drawing Sheet(s) Filed in Color)

METHOD FOR TREATING DIABETIC RETINOPATHY

CROSS REFERENCE TO RELATED APPLICATIONS

This is a divisional application of U.S. patent application Ser. No. 14/632,653 filed on Feb. 26, 2015.

BACKGROUND OF THE INVENTION

1. Field of the Invention

The present invention relates to a herbal composition and, more particularly, to a herbal composition for relieving symptoms of diabetic retinopathy. The present invention further relates to a method for relieving symptoms of diabetic retinopathy by administrating the herbal composition to a subject in need.

2. Description of the Related Art

Diabetic retinopathy is a complication of diabetes, which is caused by hyperglycemia-induced incompetence of the vascular walls, resulting in microvascular retinal changes, such as dysfunction of blood-retinal barrier and hyperpermeability of capillary circulation. Moreover, diabetic retinopathy is the leading cause of blindness in patients with diabetes.

Conventional methods for relieving symptoms of diabetic retinopathy include laser surgery, vitrectomy and intraocular injection of corticosteroids. However, all of the conventional methods belong to invasive treatments but cannot completely cure diabetic retinopathy. Therefore, patients with diabetic retinopathy have to monitor blood glucose level to adapt to maintain normal blood glucose level (euglycemia) all the time. Furthermore, intraocular injection of corticosteroids can also lead to side effects such as steroid-induced disorders. In light of this, it is necessary to improve the conventional method for relieving symptoms of diabetic retinopathy.

*Dendrobium officinale* not only can be used to lower the blood glucose level, improving diabetes-related disorders, but also can be used as the active ingredient for retinal disorders. However, *Dendrobium officinale* cannot be used for relieving symptoms of diabetic retinopathy effectively.

SUMMARY OF THE INVENTION

It is therefore the objective of this invention to provide a method for relieving symptoms of diabetic retinopathy without side effects lead by the conventional methods.

A method for relieving symptoms of diabetic retinopathy includes administering a herbal composition to a subject in need thereof to relieve symptoms of diabetic retinopathy, wherein the herbal composition comprises 40 wt % of an ethanol extract of *Astragalus membranaceus,* 8 wt % of an ethanol extract of *Angelica sinensis* and 52 wt % of a water extract of *Dendrobium officinale.*

In a preferred form shown, the herbal composition is administered to the subject in need thereof in a dosage of 100 mg/per kilogram of body weight per day for 15-60 days.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
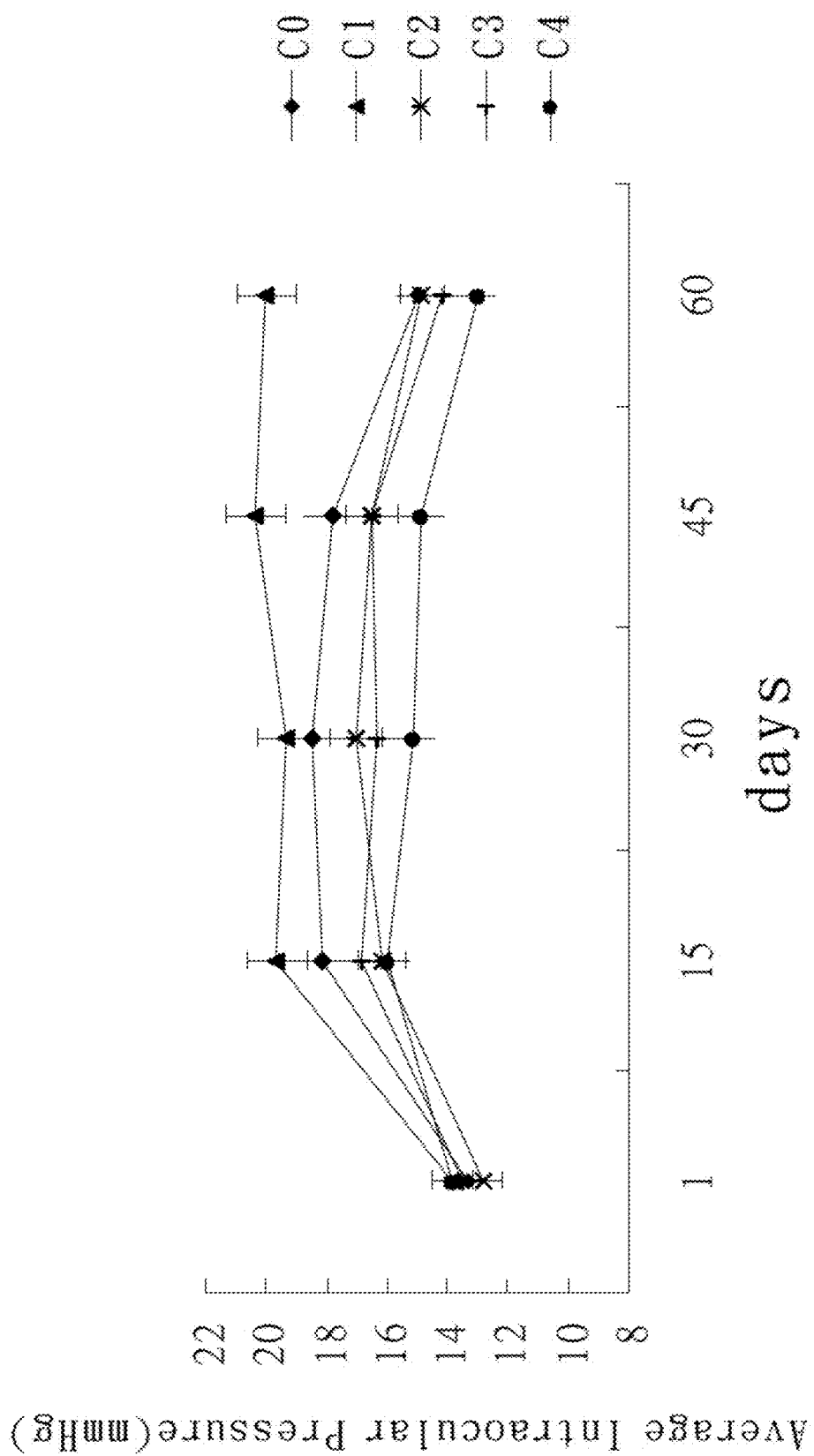
FIG. 1 depicts a line graph illustrating intraocular pressure of rats (groups C0-C4) on day 1, day 15, day 30, day 45 and day 60.
Figure 2A:
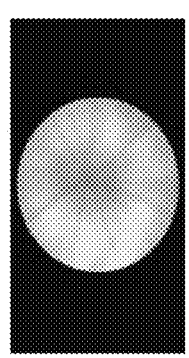
FIG. 2a depicts a fundus photograph of rat (group C0) on day 1.
Figure 2B:
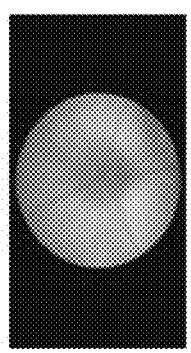
FIG. 2b depicts a fundus photograph of rat (group C0) on day 15.
Figure 2C:
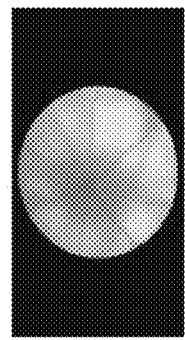
FIG. 2c depicts a fundus photograph of rat (group C0) on day 30.
Figure 2D:
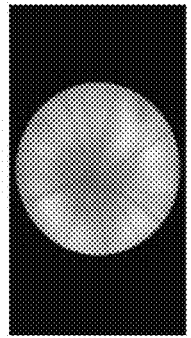
FIG. 2d depicts a fundus photograph of rat (group C0) on day 45.
Figure 2E:
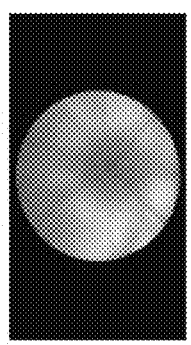
FIG. 2e depicts a fundus photograph of rat (group C0) on day 60.
Figure 3A:
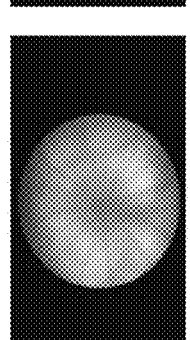
FIG. 3a depicts a fundus photograph of rat (group C1) on day 1.
Figure 3B:
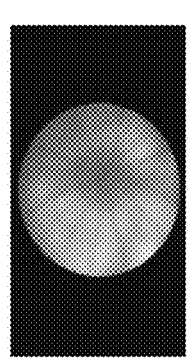
FIG. 3b depicts a fundus photograph of rat (group C1) on day 15.
Figure 3C:
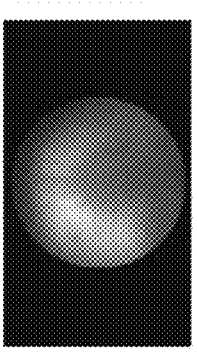
FIG. 3c depicts a fundus photograph of rat (group C1) on day 30.
Figure 3D:
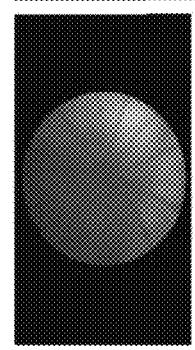
FIG. 3d depicts a fundus photograph of rat (group C1) on day 45.
Figure 3E:
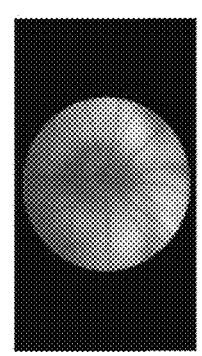
FIG. 3e depicts a fundus photograph of rat (group C1) on day 60.
Figure 4A:
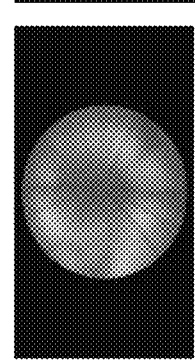
FIG. 4a depicts a fundus photograph of rat (group C2) on day 1.
Figure 4B:
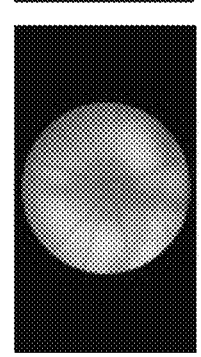
FIG. 4b depicts a fundus photograph of rat (group C2) on day 15.
Figure 4C:
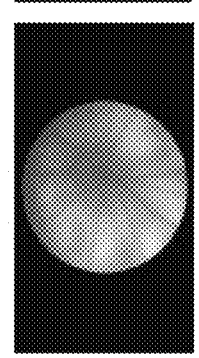
FIG. 4c depicts a fundus photograph of rat (group C2) on day 30.
Figure 4D:
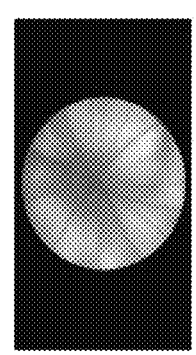
FIG. 4d depicts a fundus photograph of rat (group C2) on day 45.
Figure 4E:
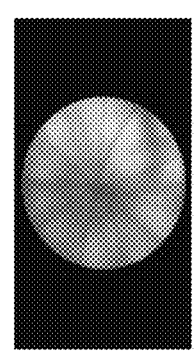
FIG. 4e depicts a fundus photograph of rat (group C2) on day 60.
Figure 5A:
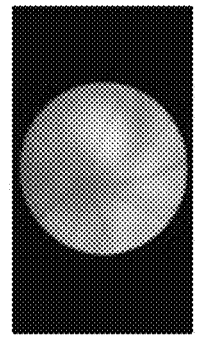
FIG. 5a depicts a fundus photograph of rat (group C3) on day 1.
Figure 5B:
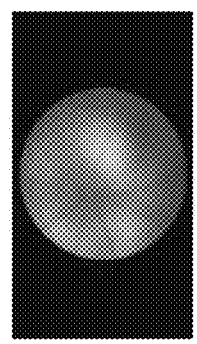
FIG. 5b depicts a fundus photograph of rat (group C3) on day 15.
Figure 5C:
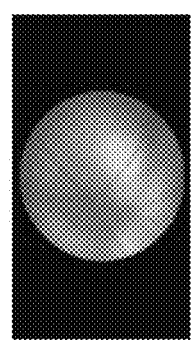
FIG. 5c depicts a fundus photograph of rat (group C3) on day 30.
Figure 5D:
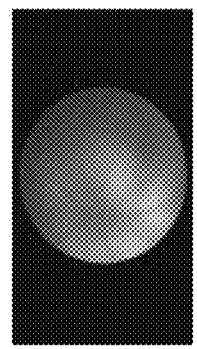
FIG. 5d depicts a fundus photograph of rat (group C3) on day 45.
Figure 5E:
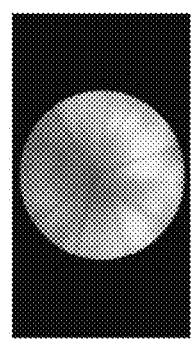
FIG. 5e depicts a fundus photograph of rat (group C3) on day 60.
Figure 6A:
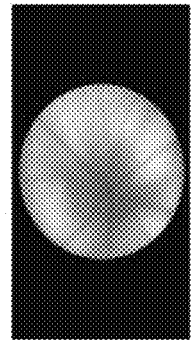
FIG. 6a depicts a fundus photograph of rat (group C4) on day 1.
Figure 6B:
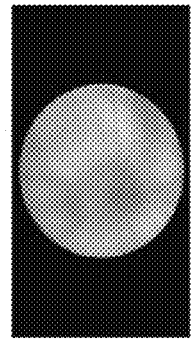
FIG. 6b depicts a fundus photograph of rat (group C4) on day 15.
Figure 6C:
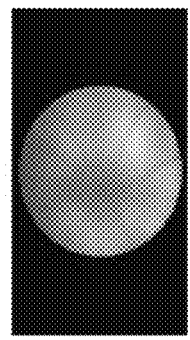
FIG. 6c depicts a fundus photograph of rat (group C4) on day 30.
Figure 6D:
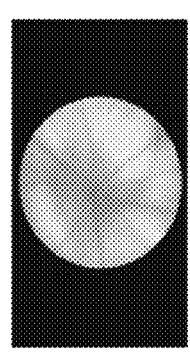
FIG. 6d depicts a fundus photograph of rat (group C4) on day 45.
Figure 6E:
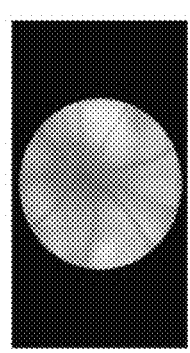
FIG. 6e depicts a fundus photograph of rat (group C4) on day 60.

An embodiment of a herbal composition for relieving symptoms of diabetic retinopathy according to preferred teachings of the present invention includes 40 wt % of an ethanol extract of *Astragalus membranaceus*, 8 wt % of an ethanol extract of *Angelica sinensis* and 52 wt % of a water extract of *Dendrobium officinale*. With such performance, the herbal composition rich in indicator ingredients such as ferulic acid and polysaccharides can effectively relieve symptoms of diabetic retinopathy.

The method to manufacture the ethanol extract of *Astragalus membranaceus*, the ethanol extract of *Angelica sinensis* and the water extract of *Dendrobium officinale* are the prior art well-known in the field, and therefore are not limited to the following statement. As an example, the ethanol extract of *Astragalus membranaceus* is manufactured by extracting a root sample of *Astragalus membranaceus* with 95% ethanol, while the ethanol extract of *Angelica sinensis* is manufactured by extracting a root sample of *Angelica sinensis* with 95% ethanol. In this embodiment, the root sample of *Astragalus membranaceus* (1 kg) is mixed with the root sample of *Angelica sinensis* (200 g), followed by extracting with 95% ethanol (4 L.)

Moreover, the water extract of *Dendrobium officinale* is manufactured by extracting a stem sample of *Dendrobium officinale* with water. For example, the stem sample of *Dendrobium officinale* can be extracted with water at 50-80° C., followed by partitioning with 95% ethanol at 50-80° C. to obtain a precipitate as the water extract of *Dendrobium officinale*. In this embodiment, the stem sample of *Dendrobium officinale* (1 kg) is mixed and extracted with heated water (4 L) for 2 hours. The obtained solution is vacuum-concentrated (final volume to 1 L), followed by partitioning with pre-cooled 95% ethanol (3 L, 4° C.) overnight. The water extract of *Dendrobium officinale* is obtained as a precipitate after centrifugation at 12,000 rpm for 20 minutes, followed by removing the supernatant.

The herbal composition according to the present invention can effectively recover the hyperglycemia-induced damages and relieve symptoms of diabetic retinopathy, thereby being potential to be applied to pharmaceutical industry, being an active ingredient of medication or health products for relieving symptoms of diabetic retinopathy. In the present invention, the herbal composition can be given to any subject in need individually or combined with any acceptable excipients, for example carriers or other ingredients, and is capable of being further manufactured into any form of medicament, such as pill, capsule, powder, solution and pastil for easy and convenient delivery to the subject in need.

In addition, the herbal extract can be administered to the subject in need thereof. For example, the herbal composition can be administered to the subject in need thereof in a dosage of 100 mg/per kilogram of body weight per day (100 mg/kg/day) for 15-60 days. Therefore, ferulic acid and polysaccharides rich in the herbal composition poses synergistic effect in the subject in need thereof, recovering the hyperglycemia-induced damages and relieving symptoms of diabetic retinopathy.

In order to evaluate the herbal composition poses effect on relieving symptoms of diabetic retinopathy, the following trials are carried out.

Trial (A): Manufacturing Procedure.

In trial (A), The root sample of *Astragalus membranaceus* (1 kg) is mixed with the root sample of *Angelica sinensis* (200 g), followed by extracting with 95% ethanol (4 L) for 800 minutes. The extraction process repeats for 3 times, and the resulting product is vacuum filtrated, vacuum concentrated, and freeze-dried to obtain 98.52 g of an extract mixture containing the ethanol extract of *Astragalus membranaceus* and the ethanol extract of *Angelica sinensis*.

On the other hand, water (4 L) is mixed with the stem sample of *Dendrobium officinale* (1 kg), and heated to extract the stem sample of *Dendrobium officinale* for 2 hours. The obtained solution is vacuum concentrated (final volume to 1 L) and partitioned with pre-cooled 95% ethanol (3 L, 4° C.) overnight. Then, 74.58 g of the water extract of *Dendrobium officinale* (as the precipitate) is obtained after by centrifugating at 12,000 rpm for 20 minutes and removing the supernatant.

The extract mixture and the water extract of *Dendrobium officinale* is mixed to obtain the herbal composition according to the present invention, which includes 40 wt % of the ethanol extract of *Astragalus membranaceus*, 8 wt % of the ethanol extract of *Angelica sinensis* and 52 wt % of the water extract of *Dendrobium officinale*.

Trial (B): Indicator Ingredients.

For analyzing ferulic acid, the herbal composition (1.608 g) is dissolved in methanol, filtrated by the 0.45 μm filter, and adjusted the final volume to 10 mL. Moreover, Thermo ODS Hypersil (5 μm) 250 mm×4.6 mm column is used. A mobile phase is acetonitrile and 0.05% phosphoric acid mixed in a volumetric ratio of 18:82. A flow rate of the mobile phase is 1 mL/min. An absorbance at 320 nm is used to determine the percentage of the total area of ferulic acid. The content of ferulic acid calculated according to the standard curve is 42.255±5.655 μg/g.

For analyzing polysaccharides, the phenol-sulfuric acid method is carried out. In detail, the herbal composition is dissolved in hot water in a concentration of 200 mg/100 mL. The diluents with volume of 0.3 mL, 0.4 mL, 0.5 mL, 0.6 mL, 0.7 mL and 0.8 mL are mixed with phenol solution (1× volume, 5%), and then subjected to 5× volume of a direct stream of concentrated sulfuric acid. After cooling for 30 minutes, absorbance at 490 nm is measured. The content of polysaccharides calculated according to the standard curve is 14.667 μg/g in a form of glucose content per gram of the herbal composition.

Trial (C): Effects on Diabetic Retinopathy In Vivo.

Wistar male rats (6-8 week-old, weight 150-200 g) purchased from The National Laboratory Animal Center (NLAC) are used in trial (C). The rats are housed in an animal room in the Experimental Animal Center of Tajen university with constant temperature of 24±2° C., with relative humidity of 65±2%, where is kept on a 12-hours light and 12-hours dark cycle. The rats are housed and kept on free diet and water.

Rats with type I diabetes (groups C1-C4 shown in TABLE 1) are induced by administration of streptozotocin (STZ, 60 mg/kg) via intraperitioneal injection after fasting for 72 hours. Moreover, after administration of STZ for 72 hours, the rats with type I diabetes show blood sugar level higher than 300 mg/L and symptoms including frequent urination, increased thirst and increased hunger.

Referring to TABLE 1, rats of groups C2-C4 are orally administered with the extract mixture containing the ethanol extract of *Astragalus membranaceus* and the ethanol extract of *Angelica sinensis* (group C2, 50 mg/kg/day), the water extract of *Dendrobium officinale* (group C3, 50 mg/kg/day) and the herbal composition (group C4, 100 mg/kg/day) for 60 days, respectively. Intraocular pressure (IOP) and symptoms of diabetic retinopathy are monitored on day 1, day 15, day 30, day 45 and day 60.

TABLE 1

| Groups | STZ induction | Treatment (dosage per day) |
| --- | --- | --- |
| C0 | − | Water (1 mL/kg) |
| C1 | + | Water (1 mL/kg) |
| C2 | + | Extract mixture (50 mg/kg) |
| C3 | + | Water extract of *Dendrobium officinale* (50 mg/kg) |
| C4 | + | Herbal composition (100 mg/kg) |

The intraocular pressure of the rats of groups C0-C4 on day 1, day 15, day 30, day 45 and day 60 are monitored after anesthetizing with diethyl ether, respectively. As shown in FIG. 1, the intraocular pressure of group C1 remains about 20 mmHg after day 15, while the intraocular pressure of group C4 (administered with the herbal composition) is significantly decreased.

Moreover, fundus photography is carried with MiiS Horus Scope DOC100 on day 1, day 15, day 30, day 45 and day 60, after administrating of atropine (0.25%), followed by anesthetizing with diethyl ether. Fundus photographs are shown as FIGS. 2a-2e (group C0), 3a-3e (group C1), 4a-4e (group C2), 5a-5e (group C3) and 6a-6e (group C4).

Referring to FIGS. 2a-2e, rats of group C0 show no symptoms of diabetic retinopathy, while rats of group C1 show symptoms of diabetic retinopathy, such as intraretinal microvascular abnormalities (IRMA) and retinal hemorrhage after day 30 referring to FIGS. 3a-3e. Moreover, referring to FIGS. 4a-4e and FIGS. 5a-5e, although rats of groups C2 and C3 also show symptoms of diabetic retinopathy, the symptoms of diabetic retinopathy is slighter than the symptoms of diabetic retinopathy in rats of groups C1. Finally, referring to FIGS. 6a-6e, rats of group C4, similar to rats of group C0, show no symptoms of diabetic retinopathy. That is, the herbal composition according to the present invention can be used to relieve symptoms of diabetic retinopathy.

In summary, the herbal composition for relieving symptoms of diabetic retinopathy according to the present invention, rich in indicator ingredients such as ferulic acid and polysaccharides, is capable of relieving symptoms of relieving symptoms of diabetic retinopathy, and therefore, the herbal composition for relieving symptoms of diabetic retinopathy according to the present invention can be used to slow or stop further vision loss.

Furthermore, the method according to the present invention is a more acceptable, non-invasive treatment, by administering the herbal composition rich in indicator ingredients such as ferulic acid and polysaccharides, further preventing from side effects such as steroid-induced disorders.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating diabetic retinopathy comprising administering to a subject in need thereof an effective amount of an herbal composition, wherein the herbal composition comprises:

40 wt % of an ethanol extract of *Astragalus membranaceus*, 8 wt % of ethanol extract of *Angelica sinensis*, and 52 wt % of a water extract of *Dendrobium officinale*.

2. The method treating diabetic retinopathy as claimed in claim 1, wherein the herbal composition is administered to the subject in need thereof in a dosage of 100 mg/per kilogram of body weight per day for 15-60 days.

* * * * *